(12) United States Patent
Elder et al.

(10) Patent No.: US 7,618,697 B2
(45) Date of Patent: Nov. 17, 2009

(54) CARBOXYLIC ACID ESTERS OF ZOSTERIC ACID FOR PREVENTION OF BIOFOULING

(75) Inventors: Stewart Todd Elder, Butler, NJ (US); Fadi Khawam, Norwood, NJ (US); Andrea Preuss, Basel (CH); Jürgen Wiethan, Emmendingen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 478 days.

(21) Appl. No.: 11/524,980

(22) Filed: Sep. 21, 2006

(65) Prior Publication Data

US 2007/0128151 A1 Jun. 7, 2007

Related U.S. Application Data

(60) Provisional application No. 60/720,662, filed on Sep. 26, 2005.

(51) Int. Cl.
*B32B 9/04* (2006.01)
(52) U.S. Cl. .................................................. 428/68

(58) Field of Classification Search .................. 428/68, 428/76, 543, 907; 424/78.09
See application file for complete search history.

(56) References Cited

U.S. PATENT DOCUMENTS

| 5,384,176 A * | 1/1995 | Zimmerman et al. .......... 428/68 |
| 5,607,741 A | 3/1997 | Zimmerman et al. .......... 428/68 |
| 6,790,910 B1 | 9/2004 | Sosna et al. .................. 525/191 |

* cited by examiner

*Primary Examiner*—Michael G Hartley
*Assistant Examiner*—Jagadishwar R Samala
(74) *Attorney, Agent, or Firm*—Joseph C. Suhadolnik

(57) ABSTRACT

Carboxylic acid ester derivatives of zosteric acid are effective in preventing biofouling and are readily formulated into coatings or films. Coating or film compositions of the esters, and methods for their application, are provided which reduce the dissolution of the esters into water or loss to the environment. The Zosteric acid esters of the invention appear to function by preventing adhesion of an organism to a surface rather than by acute toxic activity rendering said compositions more environmentally acceptable.

20 Claims, No Drawings

CARBOXYLIC ACID ESTERS OF ZOSTERIC ACID FOR PREVENTION OF BIOFOULING

This application claims benefit under 35 USC 119(e) of U.S. provisional application No. 60/720,662, filed Sep. 26, 2005.

This invention provides compounds, compositions and methods of using said compositions that prevent the adhesion of organisms to surfaces.

Surfaces in contact with marine environments (which include fresh water, brackish water and salt water environments) are known to become fouled by various types of microorganisms and macro organisms. Vulnerable surfaces include, for example, the hulls of ships, surfaces of docks or the inside of pipes in circulating or pass-through water systems. Attaching themselves to these surfaces, organisms not only impede water flow across the surface hampering performance, but can also cause deterioration of the surface itself.

The control of biofouling on artificial surfaces is a significant problem for structures in contact with the marine environment. Subsequent to the removal of environmentally hazardous organo-tin compounds from antifouling paints, control of biofouling accumulation has become the single most expensive maintenance problem incurred by the U.S. Navy for ship operations.

Many other surfaces are susceptible to similar biofouling, for example walls exposed to rain water, walls of showers, roofs, gutters, pool areas, saunas, floors and walls exposed to damp environs such as basements or garages and even the housing of tools and outdoor furniture.

It is highly undesirable for organisms to become established or to spread on any of these surfaces. Slime layers frequently form, and these can lead to unsafe, unhealthy or unaesthetic conditions.

Safety concerns, however, require that any such chemical should not pose undue harm to the environment or humans. A need exists, therefore, for chemicals which combat biofouling and alleviate its adverse economic costs.

U.S. Pat. No. 6,790,910 discloses antimicrobial polymers and polymer blends obtained by polymerizing acryloxyalkylamines useful as surface coatings or protective paints and or in a process for eliminating/reducing biofouling in water systems.

Living organisms have evolved a variety of mechanisms that prevent fouling of their surfaces. Some may reduce the accumulation of fouling agents by physical means, including the sloughing of the outer tissue layer, and/or the production of an external surface that minimizes bioadhesion. The production of secondary metabolites that are capable of deterring potential fouling organisms and predators is relatively common among marine organisms.

U.S. Pat. No. 5,384,176 discloses a method for isolating zosteric acid from methanolic extracts of eelgrass and the use of zosteric acid (p-sulfoxycinnamic acid) to control biofouling on surfaces in contact with marine environments. Zosteric acid is reported not only to be effective in combating biofouling but also to be environmentally safe. Zosteric acid occurs naturally in eelgrass Zostera marina.

U.S. Pat. No. 5,607,741 discloses the activity of Zosteric acid and some analogous acids in anti-microbial assays. In addition to bacterial assays, the dose-effectiveness of ferulic acid sulfate was tested using a barnacle attachment assay. The IC-50 dose in the barnacle assay was similar to the results from the bacterial assay, suggesting a similar mode of action. These tests suggest that zosteric action prevents the attachment of organisms to a surface without necessarily being toxic towards the organism. For example, in a barnacle attachment assay, barnacles stopped swimming when exposed to the active agent, but quickly recovered when transferred to clean seawater, suggesting that attachment was prevented by a mechanism other than acute toxicity.

The suggestion is made that zosteric acid could be operating at the atomic level by blocking sulfate-binding surface sensors, or by inhibiting the polymerization of the extracellular glue.

Therefore, zosteric acid and analogues (sulfooxycinammic acid) appear to function via microbial antiadhesive effects when applied to surfaces. However, zosteric acid is very water soluble and easily washes off the surfaces or leaches out of coating.

It has been found that carboxylic acid ester derivatives of zosteric acid are effective in preventing biofouling and are readily formulated into coatings or films. The esters are less soluble in water and their application within a coating or film further reduces their dissolution into water or loss to the environment. The compositions of this invention are readily applied to a variety of surfaces and, without limiting the invention, appear to function more by preventing adhesion of an organism to a surface rather than by acute toxic activity rendering said compositions more environmentally acceptable.

DESCRIPTION OF THE INVENTION

This invention provides a composition useful in preventing biofouling of surfaces, said composition comprising a binder and a compound of formula 1.

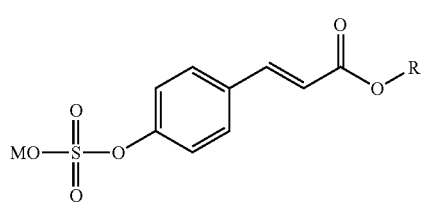

where R is $C_{1-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{5-12}$ cycloalkyl, $C_{7-12}$ aralkyl, $C_{6-10}$ aryl or a 5-10 membered heterocycle or said cycloalkyl, aralkyl, aryl or heterocycle substituted one or more times by $C_{1-4}$ alkyl, OH, $C_{1-8}$ Alkoxy, $C_{2-6}$ alkylcarboxy or halogen and M is H, a nitrogen cation, phosphorus cation or metal cation.

For example, R is $C_{2-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{6-10}$ aryl or a 5-10 membered heterocycle or said aryl or heterocycle substituted one or more times by $C_{1-4}$ alkyl, OH, $C_{1-8}$ Alkoxy, $C_{2-6}$ alkylcarboxy or halogen.

For example, R is $C_{2-24}$ alkyl, $C_{3-24}$ alkenyl, said alkyl or alkenyl substituted one or more times by $C_{1-4}$ alkyl, OH, $C_{1-8}$ alkoxy, F, Cl or Br.

For example, R is $C_{4-24}$ alkyl or $C_{3-24}$ alkenyl.

For example, M is H, an ammonium cation, an amino cation or a metal cation selected from the group of alkaline and alkaline earth metals.

For Example M is H or an ammonium, amino, Li, Na, K, Mg, Ca, Al or P cation.

Alkyl is straight or branched chain of the specified number of carbon atoms and is for example methyl, ethyl, n-propyl, n-butyl, sec-butyl, tert-butyl, n-hexyl, n-octyl, 2-ethylhexyl, n-nonyl, n-decyl, n-undecyl, n-dodecyl, n-tridecyl, n-tetradecyl, n-hexadecyl or n-octadecyl.

Alkenyl is straight or branched chain of the specified number of carbon atoms containing one or more carbon-carbon doulble bonds and is for example n-propenyl, n-butenyl, sec-butenyl, n-hexenyl, n-octenyl, n-hexadienyl, n-octadienyl, 2-ethylhexenyl, n-nonenyl, n-decenyl, n-undecenyl, n-dodecenyl, n-tridecenyl, n-tetradecenyl, n-hexadecenyl, n-octadecenyl, n-dodecadienyl, n-tetradecadienyl, n-hexadecadienyl, n-hexadecatrienyl, n-octadecadienyl, n-octadecatrienyl.

Examples of amino cations are:

unsubstituted ammonium, mono-, di-, or tri-$C_{1-4}$alkylammonium, 3-propylammonium, isopropylammonium, butylammonium, sec-butylammonium, isobutylammonium, 1,2-dimethylpropylammonium, dimethylammonium, diethylammonium, dipropylammonium, diisopropylammonium, dibutylammonium, diisobutylammonium, di-sec-butylammonium, N-methyl-N-butylammonium or N-ethyl-N-butylammonium, trimethylammonium, triethylammonium, tripropylammonium, tributylammonium, N,N-dimethylethylammonium, N,N-dimethylisopropylammonium, $C_{1-4}$alkoxy-$C_{1-4}$alkylammonium, such as 2-methoxyethylammonium, bis(2-methoxyethyl)ammonium, 3-methoxypropylammonium or ethoxypropylammonium, mono-, di- or tri-(hydroxy-$C_{1-4}$alkyl)ammonium, such as mono-, di- or tri-ethanolammonium, mono-, di- or tri-propanolammonium, mono-, di- or tri-isopropanolammonium, N-methyl- or N,N-dimethyl-ethanolammonium, -propanolammonium or -isopropanolammonium, N-methyl-diethanolammonium, -dipropanolammonium or -diisopropanolammonium, N-ethyl-diethanolammonium, -dipropanolammonium or -diisopropanolammonium, N-propyl-diethanolammonium, -dipropanolammonium or -diisopropanolammonium.

For example the amine cation is unsubstituted ammonium, diethanolammonium, triethanolammonium, dipropanolammonium, tripropanolammonium, diisopropanolammonium or triisopropanolammonium.

The antifouling esters of the invention are prepared readily from coumaric acid by esterification of the carboxyl group with an appropriate alcohol followed by reaction with chlorosulfonic acid. Other convenient methods of preparation are available.

A variety of useful, naturally occurring alcohols derived from fatty acids are available and may be used to prepare the corresponding zosterate esters, i.e., lauryl, myristyl, palmityl, stearyl, arachidyl, behenyl, lignoceryl, palmitoleyl, oleyl, linoleyl, linolenyl and arachidonyl alcohols. A mixture of alcohols may be used.

Methyl zosterate is known and displays antiadhesive effects. But it also suffers from water solubility when applied to surfaces. However, the solubility of methyl zosterate is more easily mitigated than the solubility of zosteric acid when applied in a polymeric matrix, i.e. the binder of the instant invention.

The binder may be any polymer or oligomer compatible with the present zosteric esters. The binder may be in the form of a polymer or oligomer prior to preparation of the anti fouling composition, or may form by polymerization during or after preparation, including after application to the substrate. In certain applications, such as certain coating applications, it will be desirable to crosslink the oligomer or polymer of the anti fouling composition after application.

The term binder as used in the present invention also includes materials such as glycols, oils, waxes and surfactants commercially used in the care of wood, plastic, glass and other surfaces. Examples include water proofing materials for wood, vinyl protectants, protective waxes and the like.

The antifouling composition of the invention may be a coating or a film. When the antifouling composition is a thermoplastic film which is applied to a surface, for example, by the use of an adhesive or by melt applications including calendaring and co-extrusion, the binder is the thermoplastic polymer matrix used to prepare the film.

When the antifouling composition is a coating, it may be applied as a liquid solution or suspension, a paste, gel, oil or the coating composition may be a solid, for example a powder coating which is subsequently cured by heat, UV light or other method.

As the antifouling composition of the invention may be a coating or a film, the binder can be comprised of any polymer used in coating formulations or film preparation. For example, the binder is a thermoset, thermoplastic, elastomeric, inherently crosslinked or crosslinked polymer.

Thermoset, thermoplastic, elastomeric, inherently crosslinked or crosslinked polymers include polyolefin, polyamide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyd resins, epoxy resins, unsaturated polyesters, unsaturated polyamides, polyimides, silicon containing and carbamate polymers, fluorinated polymers, crosslinkable acrylic resins derived from substituted acrylic esters, e.g. from epoxy acrylates, urethane acrylates or polyester acrylates. The polymers may also be blends and copolymers of the preceeding chemistries.

Examples of thermoplastic, elastomeric, inherently crosslinked or crosslinked polymers are listed below.

1. Polymers of mono- and di-olefins, for example polypropylene, polyisobutylene, polybutene-1, poly-4-methylpentene-1, polyisoprene or polybutadiene and also polymerisates of cyclo-olefins, for example of cyclopentene or norbornene; and also polyethylene (which may optionally be crosslinked), for example high density polyethylene (HDPE), high density polyethylene of high molecular weight (HDPE-HMW), high density polyethylene of ultra-high molecular weight (HDPE-UHMW), medium density polyethylene (MDPE), low density polyethylene (LDPE), and linear low density polyethylene (LLDPE), (VLDPE) and (ULDPE).

2. Mixtures of the polymers mentioned under 1), for example mixtures of poly-propylene with polyisobutylene, polypropylene with polyethylene (for example PP/HDPE, PP/LDPE) and mixtures of different types of polyethylene (for example LDPE/HDPE).

3. Copolymers of mono- and di-olefins with one another or with other vinyl monomers, for example ethylene/propylene copolymers, linear low density polyethylene (LLDPE) and mixtures thereof with low density polyethylene (LDPE), propylene/butene-1 copolymers, propylene/isobutylene copolymers, ethylene/butene-1 copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and copolymers thereof with carbon monoxide, or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another or with polymers mentioned under 1), for example polypropylene-ethylene/propylene copolymers, LDPE-ethylene/vinyl acetate copolymers, LDPE-ethylene/acrylic acid copolymers, LLDPE-ethylene/vinyl acetate copolymers, LLDPE-ethylene/acrylic acid copolymers and alternately or randomly structured polyalkylene-carbon monoxide copolymers and mixtures thereof with other polymers, for example polyamides.
4. Hydrocarbon resins (for example $C_5$-$C_9$) including hydrogenated modifications thereof (for example tackifier resins) and mixtures of polyalkylenes and starch.
5. Polystyrene, poly(p-methylstyrene), poly(α-methylstyrene).
6. Copolymers of styrene or α-methylstyrene with dienes or acrylic derivatives, for example styrene/butadiene, styrene/acrylonitrile, styrene/alkyl methacrylate, styrene/butadiene/alkyl acrylate and methacrylate, styrene/maleic anhydride, styrene/acrylo-nitrile/methyl acrylate; high-impact-strength mixtures consisting of styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene or styrene/ethylene-propylene/styrene.
7. Graft copolymers of styrene or α-methylstyrene, for example styrene on polybutadiene, styrene on polybutadiene/styrene or polybutadiene/acrylonitrile copolymers, styrene and acrylonitrile (or methacrylonitile) on polybutadiene; styrene, acrylonitrile and methyl methacrylate on polybutadiene; styrene and maleic anhydride on polybutadiene; styrene, acrylonitrile and maleic anhydride or maleic acid imide on polybutadiene; styrene and maleic acid imide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers, and mixtures thereof with the copolymers mentioned under 6), such as those known, for example, as so-called ABS, MBS, ASA or AES polymers.
8. Halogen-containing polymers, for example polychloroprene, chlorinated rubber, chlorinated and brominated copolymer of isobutylene/isoprene (halobutyl rubber), chlorinated or chlorosulfonated polyethylene, copolymers of ethylene and chlorinated ethylene, epichlorohydrin homo- and co-polymers, especially polymers of halogen-containing vinyl compounds, for example polyvinyl chloride, polyvinylidene chloride, polyvinyl fluoride, polyvinylidene fluoride; and copolymers thereof, such as vinyl chloride/vinylidene chloride, vinyl chloride/vinyl acetate or vinylidene chloride/vinyl acetate.
9. Polymers derived from α,β-unsaturated acids and derivatives thereof, such as polyacrylates and polymethacrylates, or polymethyl methacrylates, polyacrylamides and polyacrylonitriles impact-resistant-modified with butyl acrylate.
10. Copolymers of the monomers mentioned under 9) with one another or with other unsaturated monomers, for example acrylonitrile/butadiene copolymers, acrylo-nitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.
11. Polymers derived from unsaturated alcohols and amines or their acyl derivatives or acetals, such as polyvinyl alcohol, polyvinyl acetate, stearate, benzoate or maleate, polyvinylbutyral, polyallyl phthalate, polyallylmelamine; and the copolymers thereof with olefins mentioned in Point 1.
12. Homo- and co-polymers of cyclic ethers, such as polyalkylene glycols, polyethylene oxide, polypropylene oxide or copolymers thereof with bisglycidyl ethers.
13. Polyacetals, such as polyoxymethylene, and also those polyoxymethylenes which contain comonomers, for example ethylene oxide; polyacetals modified with thermoplastic polyurethanes, acrylates or MBS.
14. Polyphenylene oxides and sulfides and mixtures thereof with styrene polymers or polyamides.
15. Polyurethanes derived from polyethers, polyesters and polybutadienes having terminal hydroxyl groups on the one hand and aliphatic or aromatic polyisocyanates on the other hand, and their initial products.
16. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 12/12, polyamide 11, polyamide 12, aromatic polyamides derived from m-xylene, diamine and adipic acid; polyamides prepared from hexamethylenediamine and iso- and/or tere-phthalic acid and optionally an elastomer as modifier, for example poly-2,4,4-trimethylhexamethylene terephthalamide or poly-m-phenylene isophthalamide. Block copolymers of the above-mentioned polyamides with polyolefins, olefin copolymers, ionomers or chemically bonded or grafted elastomers; or with polyethers, for example with polyethylene glycol, polypropylene glycol or polytetramethylene glycol. Also polyamides or copolyamides modified with EPDM or ABS; and polyamides condensed during processing ("RIM polyamide systems").
17. Polyureas, polyimides, polyamide imides, polyether imides, polyester imides, polyhydantoins and polybenzimidazoles.
18. Polyesters derived from dicarboxylic acids and dialcohols and/or from hydroxy-carboxylic acids or the corresponding lactones, such as polyethylene terephthalate, polybutylene terephthalate, poly-1,4-dimethylolcyclohexane terephthalate, polyhydroxy-benzoates, and also block polyether esters derived from polyethers with hydroxyl terminal groups; and also polyesters modified with polycarbonates or MBS.
19. Polycarbonates and polyester carbonates.
20. Polysulfones, polyether sulfones and polyether ketones.
21. Crosslinked polymers derived from aldehydes on the one hand and phenols, urea or melamine on the other hand, such as phenol-formaldehyde, urea-formaldehyde and melamine-formaldehyde resins.
22. Drying and non-drying alkyd resins.
23. Unsaturated polyester resins derived from copolyesters of saturated and unsaturated dicarboxylic acids with polyhydric alcohols, and also vinyl compounds as crosslinking agents, and also the halogen-containing, difficultly combustible modifications thereof.
24. Crosslinkable acrylic resins derived from substituted acrylic esters, e.g. from epoxy acrylates, urethane acrylates or polyester acrylates.
25. Alkyd resins, polyester resins and acrylate resins that are crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of bisphenol-A diglycidyl ethers, bisphenol-F diglycidyl ethers, that are crosslinked using customary hardeners, e.g. anhydrides or amines with or without accelerators.

27. Mixtures (polyblends) of the afore-mentioned polymers, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

Acrylic, methacrylic and acrylamide polymers and co-polymers dispersible in water are readily used as a binder in the present invention. For example, acrylic, methacrylic and acrylamide dispersion polymers and co-polymers are used as binders in the anti-fouling coatings.

Biocompatible coating polymers, such as, poly[-alkoxyalkanoate-co-3-hydroxyalkenoate] (PHAE) polyesters, Geiger et. al. Polymer Bulletin 52, 65-70 (2004), can also serve as binders in the present invention.

Alkyd resins, polyesters, polyurethanes, epoxy resins, silicone containing polymers, fluorinated polymers and polymers of vinyl acetate, vinyl alcohol and vinyl amine are non-limiting examples of common coating binders useful in the present invention. Other coating binders, of course, are part of the present invention.

Coatings are frequently crosslinked with, for example, melamine resins, urea resins, isocyanates, isocyanurates, polyisocyanates, epoxy resins, anhydrides, poly acids and amines, with or without accelerators.

The anti-fouling compositions of present invention are for example a coating applied to a surface which is exposed to conditions favorable for bioaccumulation. The presence of the compounds of formula 1 in said coating will prevent the adherence of organisms to the surface.

The anti-fouling composition of the present invention may be part of a complete coating or paint formulation, such as a marine gel-coat, shellac, varnish, lacquer or paint, or the anti fouling composition may comprise only a compound of formula 1 and binder, or a compound of formula 1, binder and a carrier substance. It is anticipated that other additives encountered in such coating formulations or applications will find optional use in the present applications as well.

The coating may be solvent borne or aqueous. Aqueous are typically considered more environmentally friendly.

The coating is, for example, aqueous dispersion of a compound of formula 1 and a binder or a water based coating or paint. For example, the coating comprises an aqueous dispersion of a compound of formula 1 and an acrylic, methacrylic or acrylamide polymers or co-polymers or a poly[-alkoxyalkanoate-co-3-hydroxyalkenoate]polyester.

The coating is, for example, a coating or varnish used in marine applications.

The coating may be applied to a surface which has already been coated, such as a protective coating, a clear coat or a protective wax applied on top of a previously coated article.

Coating systems include marine coatings, wood coatings, other coatings for metals and coatings over plastics and ceramics. Exemplary of marine coatings are gel coats comprising an unsaturated polyester, a styrene and a catalyst.

The coating is, for example a house paint, or other decorative or protective paint. It may be a paint or other coating that is applied to cement, concrete or other masonry article. The coating may be a water proofer as for a basement or foundation.

As the anti-fouling composition is intended for use in maritime applications as well as near pool areas etc., the composition may be part of a non-skid coating including coatings for stairs, paths and handrails.

The coating composition is applied to a surface by any conventional means including spin coating, dip coating, spray coating, draw down, or by brush, roller or other applicator. A drying or curing period will typically be needed.

Coating or film thickness will vary depending on application and will become apparent to one skilled in the art after limited testing.

The anti-fouling composition may be in the form of a protective laminate film.

Such a film typically comprises thermoset, thermoplastic, elastomeric, or crosslinked polymers. Examples of such polymers include, but are not limited to, polyolefin, polyamide, polyurethane, polyacrylate, polyacrylamide, polycarbonate, polystyrene, polyvinyl acetates, polyvinyl alcohols, polyester, halogenated vinyl polymers such as PVC, natural and synthetic rubbers, alkyd resins, epoxy resins, unsaturated polyesters, unsaturated polyamides, polyimides, fluorinated polymers, silicon containing and carbamate polymers. The polymers may also be blends and copolymers of the preceeding chemistries.

When the anti-fouling composition is a preformed film it is applied to the surface by, for example, the use of an adhesive, or co-extruded onto the surface. It may also be mechanically affixed via fasteners which may require the use of a sealant or caulk wherein the esters of the instant invention may also be advantageously employed.

A plastic film may also be applied with heat which includes calendaring, melt applications and shrink wrapping.

The anti-fouling composition may be part of a polish, such a furniture polish, or a dispersant or surfactant formulation such as a glycol or mineral oil dispersion or other formulation as used in for example wood protection.

Examples of useful surfactants include, but are not limited to, polyoxyethylene-based surface-active substances, including polyoxyethylene sorbitan tetraoleate (PST), polyoxyethylene sorbitol hexaoleate (PSH), polyoxyethylene 6 tridecyl ether, polyoxyethylene 12 tridecyl ether, polyoxyethylene 18 tridecyl ether, and the polyoxyethlene-polyoxypropylene copolymers. Other matrix-forming components include dextrans, linear PEG molecules (MW 500 to 5,000,000), star-shaped PEG molecules, comb-shaped and dendrimeric, hyperbrached PEG molecules, as well as the analogous linear, star, and dendrimer polyamine polymers, and various carbonated, perfluorinated and siliconated surfactants.

Given the wide array of applications for the present anti-fouling compositions, the composition may contain other additives such as antioxidants, UV absorbers, hindered amines, phosphites or phosphonites, benzofuran-2-ones, thiosynergists, polyamide stabilizers, metal stearates, nucleating agents, fillers, reinforcing agents, lubricants, emulsifiers, dyes, pigments, dispersents, other optical brighteners, flame retardants, antistatic agents, blowing agents and the like, such as the materials listed below, or mixtures thereof.

1. Antioxidants 1.1. Alkylated phenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1-methylheptadec-1-yl) phenol, 2,4-dimethyl-6-(1-methyltridec-1-yl)phenol, propyl gallate and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(□-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis [6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3-tert-butyl-4-hydroxyphenyl) butyrate], bis(3-tert-butyl-4-hydroxy-5-methyl-phenyl)dicyclopentadiene, bis[2-(3'tert-butyl-2-hydroxy-5-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)4-n-dodecylmercaptobutane, 1,1,5,5-tetra-(5-tert-butyl-4-hydroxy-2-methylphenyl)pentane.

1.7. Benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tert-butyl-4-hydroxybenzyl) sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxy-lauric acid anilide, 4-hydroxy-stearic acid anilide, 2,4-bis-octylmercapto-6-(3,5-tert-butyl-4-hydroxyanilino)-s-triazine and octyl-N-(3,5-di-tert-butyl-4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis (4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905, 4,853,471; 5,268,450; 5,278,314; 5,280,124; 5,319,091; 5,410,071; 5,436,349; 5,516,914; 5,554,760; 5,563,242; 5,574,166; 5,607,987 and 5,977,219, such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy)carbonyl-ethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3,5-di-α-cumylphenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzo-triazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butyl-phenyl)-2H-benzotriazole, 5-trifluoromethyl-2-(2-hydroxy-3,5-di-t-butylphenyl)-2H-benzo-triazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3,5-di-t-butylphenyl)-2H-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, dimethyl p-methoxybenzylidenemalonate or di-(1,2,2,6,6-pentamethylpiperidin-4-yl) p-methoxybenzylidenemalonate.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, bis(2,2,6,6-tetramethyl-4-piperidyl) sebacate, bis-(2,2,6,6-tetramethyl-4-piperidyl) succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis( 1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino) ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro[4,5]decane and epichlorohydrin, 1,1-bis-(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylenemalonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

The sterically hindered amine may also be one of the compounds described in GB-A-2301106 as component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on pages 68 to 73 of said GB-A-2301106.

The sterically hindered amine may also be one of the compounds described in EP 782994, for example compounds as described in claims 10 or 38 or in Examples 1-12 or D-1 to D-5 therein.

The sterically hindered amine may also be a hydroxylamine, hydroxylamine salt or nitroxl derivatives of hindered amine light stabilizers.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, 1-(2-hydroxy-2-methylpropoxy)-4-hydroxy-2,2,6,6-tetramethylpiperidine, 1-(2-hydroxy-2-methylpropoxy)-4-oxo-2,2,6,6-tetramethylpiperidine, bis(1-(2-hydroxy-2-methylpropoxy)-2,2,6,6-tetramethylpiperidin-4-yl) sebacate, bis(1-(2-hydroxy-2-methylpropoxy)-2,2,6,6-tetramethylpiperidin-4-yl) adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin-4-yl) glutarate and 2,4-bis{N-[1-(2-hydroxy-2-methylpropoxy)-2,2,6,6-tetramethylpiperidin-4-yl]-N-butylamino}-6-(2-hydroxyethyl-amino)-s-triazine.

2.8. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, WO 96/28431, EP 434608, EP 941989, GB 2,317,893, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, for example 4,6-bis-(2,4-dimethyl-phenyl)-2-(2-hydroxy-4-octyloxyphenyl)-s-triazine, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxyethoxy)phenyl]-6-(4-chlorophenyl)-s-triazine, 2,4-bis[2-hydroxy-4-(2-hydroxyethoxy)phenyl]-6-(2,4-dimethylphenyl)-s-triazine, 2,4-bis[2-hydroxy-4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy-4-(3-sec-amyloxy-2-hydroxy-propyloxy)phenyl]-s-triazine, 2,4-bis (2,4-dimethylphenyl)-6-[2-hydroxy-4-(3-benzyloxy-2-hydroxypropyloxy)phenyl]-s-triazine, 2,4-bis(2-hydroxy-4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)phenyl]-s-triazine, mixture of 4,6-bis-(2,4-dimethyl-phenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, 4,6-bis-(2,4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl) pentaerythritol diphosphite, bis(2,4,6-tris(tert-butylphenyl) pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl)methyl phosphite, bis(2,4-di-tert-butyl-6-methylphenyl) ethyl phosphite, 2,2',2"-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

5. Benzofuranones and indolinones, for example those disclosed in U.S. Pat. Nos. 4,325,863, 4,338,244, 5,175,312, 5,216,052, 5,252,643; DE-A-4316611; DE-A-4316622; DE-A-4316876; EP-A-0589839 or EP-A-0591102 or 3-[4-(2-acetoxy-ethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, and 3-(2,3-dimethylphenyl)-5,7-di-tert-butyl-benzofuran-2-one.

6. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine and the N,N-dialkylhydroxylamine derived from hydrogenated tallow amine.

7. Nitrones, for example N-benzyl-α-phenylnitrone, N-ethyl-α-methylnitrone, N-octyl-α-heptylnitrone, N-lauryl-α-undecylnitrone, N-tetradecyl-α-tridcylnitrone, N-hexadecyl-α-pentadecylnitrone, N-octadecyl-α-heptadecylnitrone, N-hexadecyl-α-heptadecylnitrone, N-ocatadecyl-α-pentadecylnitrone, N-heptadecyl-α-heptadecylnitrone, N-octadecyl-α-hexadecylnitrone, N-methyl-α-heptadecyinitrone and the nitrone derived from N,N-dialkylhydroxylamine derived from hydrogenated tallow amine.

8. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

11. Polyamide stabilizers, for example copper salts in combination with iodides and/or phosphorus compounds and salts of divalent manganese.

12. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium-palmitate, antimony pyrocatecholate or zinc pyrocatecholate.

13. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

14. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

15. Dispersing Agents, such as polyethylene oxide waxes or mineral oil.

16. Other additives, for example plasticizers, lubricants, emulsifiers, pigments, dyes, other optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bisbenzylidene sorbitols, benzoxazinone UV absorbers such as 2,2'-p-phenylene-bis(3,1-benzoxazin-4-one), and blowing agents.

The surface being coated or laminated is the surface of any substrate exposed to biofouling conditions. The substrate can be an inorganic or organic substrate, for example, a metal or metal alloy; a thermoplastic, elastomeric, inherently crosslinked or crosslinked polymer as described above; a natural polymer such as wood or rubber; a ceramic material; glass; leather or other textile.

The substrate may be, for example, non-metal inorganic surfaces such as silica, silicon dioxide, titanium oxides, aluminum oxides, iron oxides, carbon, silicon, various silicates and sol-gels, masonry, and composite materials such as fiberglass and plastic lumber (a blend of polymers and wood shavings, wood flour or other wood particles).

The inorganic or organic substrate is, for example, a metal or metal alloy, a thermoplastic, elastomeric, inherently crosslinked or crosslinked polymer, a ceramic material or a glass.

The substrate may be a multi-layered article comprised of the same or different components in each layer. The surface coated or laminated may be the exposed surface of an already applied coating or laminate.

The inorganic or organic substrate to be coated or laminated can be in any solid form.

For example, polymer substrates may be plastics in the form of films, injection-molded articles, extruded workpieces, fibres, felts or woven fabrics.

For example molded or extruded polymeric articles used in construction or the manufacture of durable goods such as siding, fascia and mailboxes can all benefit from the present method for stabilizer replenishment.

Plastics which would benefit from the present method include, but are not limited to, plastics used in construction or the manufacture of durable goods or machine parts, including outdoor furniture, boats, siding, roofing, glazing, protective films, decals, sealants, composites like plastic lumber and fiber reinforced composites, functional films including films used in displays as well as articles constructed from synthetic fibers such as awnings, fabrics such as used in canvas or sails and rubber articles such as outdoor matting and other uses cited in this disclosure. Exemplary of such plastics are polypropylene, polyethylene, PVC, POM, polysulfones, styrenics, polyamides, urethanes, polyesters, polycarbonate, acrylics, butadiene, thermoplastic polyolefins, ionomers, unsaturated polyesters and blends of polymer resins including ABS, SAN and PC/ABS.

The invention also provides a method of preventing biofouling of surfaces, wherein a compound of formula 1 is incorporated into a coating formulation or film which is then applied to the surface of an article.

Examples of applications of the anti-fouling compositions of the instant invention are surface coatings, protective paints, other coatings and laminates applied to vulnerable surfaces, for example, the hulls of ships, surfaces of docks or the inside of pipes in circulating or pass-through water systems, walls exposed to rain water, walls of showers, roofs, gutters, pool areas, saunas, floors and walls exposed to damp environs such as basements or garages, the housing of tools and outdoor furniture.

For example, the anti-fouling compositions of the instant invention are found, among other places, on the surfaces of:

boat hulls, docks, buoys, drilling platforms, ballast water tanks, machines, machine parts, recreational, air conditioning systems, ion exchangers, process water systems, other industrial water systems, solar-powered units, heat exchangers, sump pumps, drainage systems, roofing, basements, walls, facades, greenhouses, sheds, storage areas, awnings, garden fencing, wood protection, tent roof material, fabrics, outdoor furniture, door mats, public conveniences, bathrooms, showers, swimming pools, saunas, jointing, sealing compounds, public conveyances, locker rooms etc.

Process water includes any process water stream which is used for heating or cooling purposes in closed or open circulating systems.

This invention also provides new compounds useful in preventing the biofouling of surfaces, namely compounds of formula 1

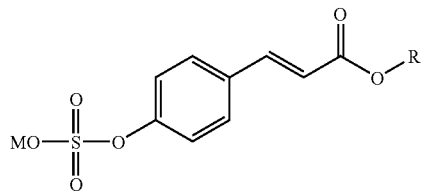

where R is $C_{1-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{5-12}$ cycloalkyl, $C_{7-12}$ aralkyl, $C_{6-10}$ aryl or a 5-10 membered heterocycle or said cycloalkyl, aralkyl, aryl or heterocycle substituted one or more times by $C_{1-4}$ alkyl, OH, $C_{1-8}$ Alkoxy, $C_{2-6}$ alkylcarboxy or halogen and M is H, a nitrogen cation, phosphorus cation or metal cation, with the proviso that R is not methyl.

For example, R is $C_{2-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{6-10}$ aryl or a 5-10 membered heterocycle or said aryl or heterocycle substituted one or more times by $C_{1-4}$ alkyl, OH, $C_{1-8}$ Alkoxy, $C_{2-6}$ alkylcarboxy or halogen.

For example, R is $C_{2-24}$ alkyl, $C_{3-24}$ alkenyl, said alkyl or alkenyl, substituted one or more times by $C_{1-4}$ alkyl, OH, $C_{1-8}$ Alkoxy, F, Cl or Br.

For example, R is $C_{4-24}$ alkyl or $C_{3-24}$ alkenyl.

For example, M is H, an ammonium cation, an amino cation or a metal cation selected from the group of alkaline and alkaline earth metals.

For Example M is H or an ammonium, amino, Li, Na, K, Mg, Ca, Al or P cation.

EXAMPLES

The following non limiting examples illustrate various aspects of the invention.

Example 1

Preparation of Methyl Coumarate

Boron trifluoride etherate (0.067 mol) is added to a solution of coumaric acid (0.034 mol) in methanol (50 ml) in a 250 ml round bottom flask and the mixture stirred at 70° C. for 2 hours and evaporated to dryness under reduced vacuum. The residual solid is taken up in $CH_2Cl_2$, washed with aqueous $NaHCO_3$, dried over $MgSO_4$ and filtered to provide, after evaporation of the $CH_2Cl_2$, the desired product as a pale yellow solid in 74.1% yield.

Example 2

Preparation of Methyl Zosterate

Chlorosulfonic acid (0.05 mol) is slowly added to a stirred solution of methyl coumarate (0.02 mol) in pyridine (25 ml) cooled at 0° C. in an ice/salt bath at such a rate as to keep the temperature below 5° C. After complete addition of the chlorosulfonic acid, the mixture is stirred for 2.5 hr at 0° C. The temperature is then raised to 40° C. and the mixture stirred overnight. The pyridine is removed under reduced pressure, distilled water (25 ml) added and the pH of the mixture raised to 9 with an aqueous solution of saturated Na$_2$CO$_3$. The mixture is evaporated to dryness and methanol is added. After filtration to remove the inorganic salts the solution is evaporated to dryness to give the desired product as a yellow solid in 69% yield.

Example 3

Preparation of Propyl Coumarate

Coumaric acid (0.030 mol) is dissolved in 1-propanol (0334 mol) in a 100 ml round bottom flask. DCC (0.033 mol) is added followed by DMAP (0.003 mol). The mixture is stirred at 50° C. for 24 hours, filtered and the propanol removed under reduced vacuum to leave an oily solid which is taken up in ethyl acetate, washed with saturated aqueous NaHCO$_3$ and distilled water, the ethyl acetate layer dried over MgSO$_4$ to leave after removal of the ethyl acetate the desired product as a pale yellow solid in 71% yield.

Example 4

Preparation of Propyl Zosterate

Chlorosulfonic acid (0.206 mol) is slowly added to a stirred solution of propyl coumarate (0.0823 mol) in pyridine (95 ml) cooled at 0° C. in an ice/salt bath at such a rate as to keep the temperature below 5° C. After complete addition of the chlorosulfonic acid, the mixture is stirred for 2.5 hr at 0° C. The temperature is then raised to 40° C. and the mixture stirred overnight. The pyridine is removed under reduced pressure, distilled water (25 ml) added and the pH of the mixture raised to 9 with an aqueous solution of saturated Na$_2$CO$_3$. The mixture is evaporated to dryness and propanol is added. After filtration to remove the inorganic salts the solution is evaporated to dryness to give the desired product as a yellow solid in 64% yield.

Example 5-7

The following zosteric esters are prepared using the procedure described in examples 3 and 4. The corresponding alcohol is used to make the coumaric ester which is followed by subsequent sulfonation.

| Example | Compound | Alcohol used | % Yield |
|---|---|---|---|
| 5 | Butyl Zosterate | 1-Butanol | 55% |
| 6 | Hexyl Zosterate | 1-Hexanol | 58% |
| 7 | Octyl Zosterate | 1-Octanol | 78% |

Example 8

Microbial Antiadhesion Assay

According to the method of Nature Medicine Vol. 6, No. 8, 1053-1056, Zosterate esters are dissolved in a solution containing an acrylate polymeric film former (Glascol LS26, 4.6% active). Test pins made of PMMA are dipped into the solutions, incubated for 20 minutes and allowed to dry. The test pins are incubated in a suspension of *Staphyloccus aureus* for 60 min, then rinsed with PBS buffer. The microbial cells adhering to the pin are detected in an immunological assay using specific antibodies against the test strain which are then detected calorimetrically. The results are reported as a percent relative to the control pins (treated with acrylate film former only), a value of 100% represents the value observed on the control pins; a value of 42% represents a 0.42× the amount of microbes found on the pins treated with acrylate film former only.

| Sample | Test Concentration | Results on PMMA Based on Control |
|---|---|---|
| Methyl zosterate | 0.50% | 28% |
| 1-Butyl zosterate | 0.50% | 70% |
| 2-Butyl zosterate | 0.50% | 42% |
| Acrylate Control | — | 100% |

What is claimed:

1. A method of protecting a surface against biofouling accumulation, comprising applying to said surface an antifouling composition comprising one or more compounds of formula 1

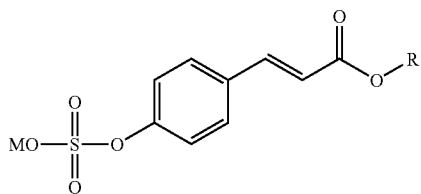

where R is $C_{1-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{5-12}$ cycloalkyl, $C_{7-12}$ aralkyl, $C_{6-10}$ aryl or a 5-10 membered heterocycle or said cycloalkyl, aralkyl, aryl or heterocycle substituted one or more times by $C_{1-4}$ alkyl, OH, $C_{1-8}$ Alkoxy, $C_{2-6}$ alkylcarboxy or halogen and M is H, a nitrogen cation, phosphorus cation or metal cation.

2. A method according to claim 1 wherein, in the compound of formula 1, R is $C_{2-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{6-10}$ aryl or a 5-10 membered heterocycle or said aryl or heterocycle substituted one or more times by $C_{1-4}$ alkyl, OH, $C_{1-8}$ alkoxy, $C_{2-6}$ alkylcarboxy or halogen.

3. A method according to claim 1 wherein, in the compound of formula 1, R is $C_{2-24}$ alkyl, $C_{3-24}$ alkenyl, said alkyl or alkenyl, substituted one or more times by $C_{1-4}$ alkyl, OH, $C_{1-8}$ Alkoxy, F, Cl or Br.

4. A method according to claim 1 wherein, in the compound of formula 1, R is $C_{4-24}$ alkyl or $C_{3-24}$ alkenyl.

5. A method according to claim 1, wherein the antifouling composition comprises a polymeric resin.

6. A method according to claim 5, wherein the antifouling composition is applied as a coating.

7. A method according to claim 5, wherein the antifouling composition is applied as a preformed film.

8. A method according to claim 2, wherein the antifouling composition comprises a polymeric resin.

9. A composition useful in preventing biofouling of surfaces, said composition comprising a binder and one or more compounds of formula 1

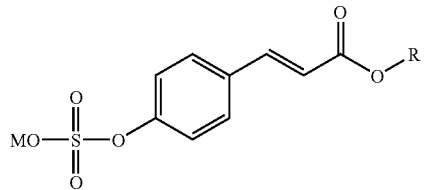

where R is $C_{1-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{5-12}$ cycloalkyl, $C_{7-12}$ aralkyl, $C_{6-10}$ aryl or a 5-10 membered heterocycle or said cycloalkyl, aralkyl, aryl or heterocycle substituted one or more times by $C_{1-4}$ alkyl, OH, $C_{1-8}$ Alkoxy, $C_{2-6}$ alkylcarboxy or halogen and M is H, a nitrogen cation, phosphorus cation or metal cation.

10. The composition of claim 9 wherein, in the compound of formula 1, R is $C_{2-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{6-10}$ aryl or a 5-10 membered heterocycle or said aryl or heterocycle substituted one or more times by $C_{1-4}$ alkyl, OH, $C_{1-8}$ Alkoxy, $C_{2-6}$ alkylcarboxy or halogen.

11. The composition of claim 9, wherein in the compound of formula 1, R is $C_{2-24}$ alkyl, $C_{3-24}$ alkenyl, said alkyl or alkenyl substituted one or more times by $C_{1-4}$alkyl, OH, $C_{1-8}$ alkoxy, F, Cl or Br.

12. The composition of claim 9, wherein in the compound of formula 1, R is $C_{4-24}$ alkyl or $C_{3-24}$ alkenyl.

13. The composition of claim 9, wherein the binder comprises a polymeric resin.

14. The composition of claim 13 which is a coating composition.

15. The composition of claim 13 which is a film composition.

16. An anti-bio-fouling compound of formula 1

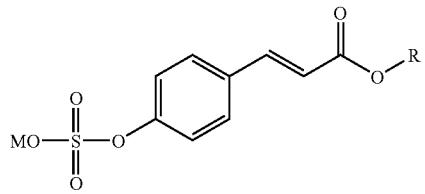

where R is $C_{1-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{5-12}$ cycloalkyl, $C_{7-12}$ aralkyl, $C_{6-10}$ aryl or a 5-10 membered heterocycle or said cycloalkyl, aralkyl, aryl or heterocycle substituted one or more times by $C_{1-4}$ alkyl, OH, $C_{1-8}$ Alkoxy, $C_{2-6}$ alkylcarboxy or halogen and M is H, a nitrogen cation, phosphorus cation or metal cation with the proviso that R is not methyl.

17. The compound of claim 16, wherein R is $C_{2-24}$ alkyl, $C_{3-24}$ alkenyl, said alkyl or alkenyl substituted one or more times by $C_{1-4}$ alkyl, OH, $C_{1-8}$ alkoxy, $C_{2-6}$alkylcarboxy or halogen or interrupted by one or more oxygen atoms or carbonyl; or R is $C_{6-10}$ aryl or a 5-10 membered heterocycle or said aryl or heterocycle substituted one or more times by $C_{1-4}$ alkyl, OH, $C_{1-8}$ Alkoxy, $C_{2-6}$ alkylcarboxy or halogen.

18. The compound of claim 16, wherein R is $C_{2-24}$ alkyl, $C_{3-24}$ alkenyl, said alkyl or alkenyl, substituted one or more times by $C_{1-4}$ alkyl, OH, $C_{1-8}$Alkoxy, F, Cl or Br.

19. The compound of claim 16, wherein R is $C_{4-24}$ alkyl or $C_{3-24}$ alkenyl.

20. The compound of claim 16, wherein M is H or an ammonium, amino, Li, Na, K, Mg, Ca, Al or P cation.

* * * * *

UNITED STATES PATENT AND TRADEMARK OFFICE
CERTIFICATE OF CORRECTION

PATENT NO. : 7,618,697 B2  Page 1 of 1
APPLICATION NO. : 11/524980
DATED : November 17, 2009
INVENTOR(S) : Elder et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 535 days.

Signed and Sealed this

Twenty-sixth Day of October, 2010

David J. Kappos
*Director of the United States Patent and Trademark Office*